United States Patent [19]

Likhosherstov et al.

[11] 3,998,820
[45] Dec. 21, 1976

[54] 10'-(ω-N-1/4-DIAZABICYCLO/-4,m,O/-ALKANYL/-ACYL)-PHENOTHIAZINES, THEIR ACIDIC ADDITION SALTS AND QUATERNARY SALTS, PROCESS FOR PRODUCING SAME AND USE

[76] Inventors: Arkady Mikhailovich Likhosherstov, Smolnaya ulitsa, 33, kv. 107; Liya Semenovna Nazarova, Petrovsko-Razumovsky proezd, 20, kv. 22; Alexandr Petrovich Skoldinov, ulitsa Alabyana, 3, korpus 1, kv. 60; Galina Alexandrovna Markova, Kotelnicheskaya naberezhnaya, 1/15, kv. 320; Natalya Veniaminovna Kaverina, Novopeschanaya ulitsa, 3, kv. 32, all of Moscow, U.S.S.R.

[22] Filed: July 1, 1974

[21] Appl. No.: 485,155

Related U.S. Application Data

[63] Continuation of Ser. No. 230,987, March 1, 1972, abandoned.

[52] U.S. Cl. .............................. 260/243 A; 424/247
[51] Int. Cl.² ..................................... G07B 279/26
[58] Field of Search .............................. 260/243 A

[56] References Cited
UNITED STATES PATENTS

| | | | |
|---|---|---|---|
| 2,512,520 | 6/1950 | Cusic | 260/243 A |
| 2,519,886 | 8/1950 | Charpentier | 260/243 A |
| 2,591,679 | 4/1952 | Cusic | 260/243 A |
| 2,694,705 | 11/1954 | Cusic | 260/243 A |
| 3,055,891 | 9/1962 | Cusic | 260/243 A |
| 3,320,246 | 5/1967 | Cusic et al. | 260/243 A |

OTHER PUBLICATIONS

Casagrande et al., Arz. Forsch., vol. 21, pp. 808-811, (1971).
Rao et al., J. Med. Chem., vol. 13, pp. 516-522, (1970).

*Primary Examiner*—John D. Randolph
*Attorney, Agent, or Firm*—Haseltine, Lake & Waters

[57] ABSTRACT

10'-[ω-N-/1,4-diazabicyclo (4,m,O)-alkanyl/-acyl]-Phenothiazines having the formula:

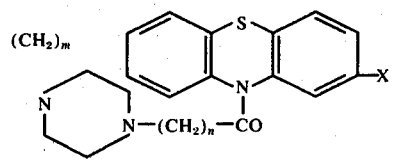

wherein X=H, Cl, or $CF_3$; $n = 1, 2$ or 3; and $m = 3$ or 5; and their pharmaceutically acceptable acidic addition and quaternary salts are pharmacologically active. The most active compound 10'-[βN-/1,4-diazabicyclo-(4,3,0)-nonanyl/-propionyl]-2'-chlorophenothiazine of the formula:

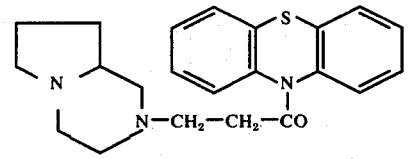

is useful as the active ingredient of a medicated compound possessing spasmolytic and coronary-dilatant effect.

The process for producing said compounds comprises reacting an ω-chloracyl -2-substituted phenothiazine with a 1, 4-diazabicyclo-(4,m,O)-alaken in an inert solvent medium at a temperature of 50°-140° C followed by isolation of the desired product.

5 Claims, No Drawings

10'-[ω-N-(1,4-DIAZABICYCLO-[4,m,o]-ALKANYL)-ACYL]-PHENOTHIAZINES, THEIR ACIDIC ADDITION SALTS AND QUATERNARY SALTS, PROCESS FOR PRODUCING SAME AND USE

This application is a continuation of applicants' copending application Ser. No. 230,987, filed Mar. 1, 1972, now abandoned.

The present invention relates to a process for producing a novel compound, viz. a 10'-[ω-N-(1,4-diazabicyclo-[4,m,o]-alkanyl)-acyl)-phenothiazine and a pharmaceutically acidic addition and quaternary salt thereof.

Said compounds correspond to the following general formula:

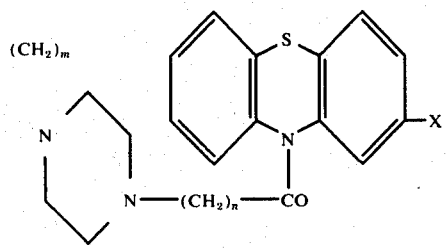

wherein X=H, Cl, or $CF_3$; n=1, 2, or 3; and m= 3 or 5.

The compounds according to the present invention and their pharmaceutically acceptable acidic addition and quaternary salts possess pharmacological activity and show spasmolytic and coronary-dilatant properties.

The novel compounds according to the present invention are solids or, in most cases, high-boiling oils.

Salts of said compounds are crystalline powders having white or cream-white color. They are well-soluble in water, aqueous alcohol, but insoluble in ether, chloroform and other organic solvents.

Said compounds possess spasmolytic and coronary-dilatan properties, whereby they have found a wide application in me dicine.

The process for producing said compounds, according to the invention, comprises reacting ω-chloracyl-2-substituted phenothiazines with 1,4-diazabicyclo-4(m,o)-alkanes in an inert organic solvent medium at a temperature of 50°–140° C followed by isolation of the desired product.

The most active compound is 10'-(β-N-/1,4-diazabicyclo-(4,3,0)-nonanyl/-propyonyl)-2'-chlorophenothiazin of the formula:

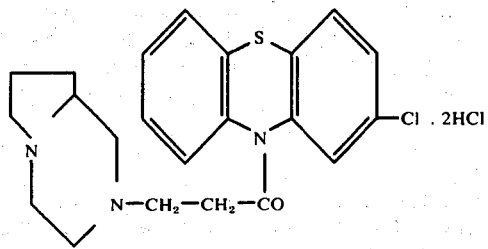

This compound of the present invention is an active principle of a medicated compound possessing coronary-dilatant and spasmolytic action, which compound is referred to hereinafter as nonachlazine.

The medicated compound is employed for cutting short stenocardia attacks as well as for treating seriously ill coronary patients during the exacerbation period. The indication for application of the medicated compound is ischemic heart disease of all, the three stages; stenocardia attacks; cardiac muscle infarction.

Pharmacological studies have shown that the medicated compound possesses a pronounced vascular dilatant action, mainly upon the coronal artery system.

Experiments carried out on cats and rats have demonstrated that the medicated compound when intravenously injected at a rate of 5–7 mg./kg considerably improves the blood supply of the heart, thereby increasing the coronary blood flow by 120% for 30–60 minutes. The level of arterial system pressure is not substantially changed therewith.

Oxygen consumption by the heart is increased in parallel with the growth of coronary blood flow under the influence of the medicated compound. As has been revealed by further studies relating to registration of coronary vascular resistance by the resistography method, the effect of the medicated compound of the present invention is connected with its direct influence upon coronary vascular tone. Under the influence of the medicated compound a reduction of coronal vascular resistance by 25–35% (average) is observed.

The medicated compound does not result in electrocardiagram changes, nor does it noticeably affect the vegetative nervous system and the central nervous system.

The compound is only slightly toxic and has sufficiently wide range of a therapeutic action. During the study of a sharp toxicity of the medicated compound it has been found that upon intravenous infusion thereof to white mice having 23–26 g. body weight, the $LD_{50}$ is 55 mg./kg.

The medicated compound of the present invention possesses a spasmolytic action eliminating the spasm of intestianl smooth musculature caused by barium chloride.

By the intensiveness of its coronary-dilatant action the medicated compound of the present invention is superior to 2-chloro-10-(β-diethylaminopropyonyl)-phenothiazine chlorohydrate, persantine, papaverine, segoptine, intensaine, and nitroglycerol.

The medicated compounds have been clinically tested in six clinics on 300 patients.

The compound was prescribed at a rate of 30 mg. three times per day to patients with angina pectoris exacerbation and frequent stenocardia attacks relieved only by narcotics; to patients with fresh cardiac muscle infarction accompanied by frequent attacks and pains, to patients with fresh small-seat necrosis, and to seriously ill coronary patients during the exacerbation period.

There has been observed a good endurance of the compound by the patients; there have been no side-effects upon the application of the compound. The compound has been well borne by patients with tachycardia and bradycardia, and also with ulcer disease and cholecystitis. No changes of arterial pressure have been observed. Neither have there been observed changes in the blood and urine, during the application of the compound. There have been no gastritic complaints. Also there have been no observed electrocardiogram deviations due to the application of the medicated compound. One of the criteria for evaluating the effectiveness of the compound was the amount of nitroglycerol tablets taken daily in the beginning and at the end of the treating. The number of nitroglycerol tablets have been reduced more than twice upon combined application with the compound.

It has been noted that in 104 of 108 cases of stenocardia, the pains were completely releived or became weak and rare after taking the medicated compound. In 2 of the cases where the attacks of pain remained, the pain could not be relieved even by nitroglycerol. In 17 cases, the treatment was effected by alternately using the compound at a rate of 30 mg. three times per day for four days and then using a placebo at a rate of 0.00 g. three times per day for 4 days.

The placebo was employed until there was complete disappearance of pains owing to the compound. The results of treatment with placebo after the application of the medicated compound of the present invention are given in the following table.

| Number of patients | Frequency of stenocardia attacks | | | |
|---|---|---|---|---|
| | 1st day | 2nd day | 3rd day | 4th day |
| 5 | — | 1 | 2–3 | 2–3 |
| 6 | — | 2 | 3–4 | 2–3 |
| 6 | 1 | 3 | 3–4 | 4–5 |

When the employing placebo was employed, the pain attacks returned, which proves the absence of an after-action of the compound and its obvious efficiency.

By its efficiency of action and rapidity of effect, it can manifestly be seen that the medicated compounds of the present invention are superior to many other remedies used to treatment of exacerbation of ischemic heart disease such as papaverine, inderal, intensaine, isoptine, 2-chloro-10-($\beta$-diethylaminopropyonyl)-phenothiazine chlorohydrate, corontine and the like. Application of this compound is indicated at the beginning of an exacerbation period of coronary disease with frequent and lasting pains. Under the influence of the compound of the present invention patients easily overcome a dangerous period of the disease exacerbation. Further, after the period during which the pains have been reduced or have disappeared has stabilized it is possible to give the patients other medicines possessing an after-action, i.e. residual effect. It is also possible to use a combined treatment with the compound and 2-chloro-10-($\beta$-diethylaminoproponyl)-phenothiazine chlorohydrate, nitroglycerol, or intensaine or medicated compounds of the inderal-isoptine group.

The medicated compound of the present invention, freeing patients from stenocardia attacks that are to curtail or stop difficult stenocardia attacks, makes it possible to help patients out of an exacerbation period without development of necrosis.

The medicated compound of the present invention can be employed as is in a powder-like form.

According to the invention, the medicated compound may contain the active principle in combination with a pharmaceutical by acceptable filler or carrier.

A preferred pharmaceutical carrier is starch or powdered sugar in which the active principle content is 15–90 mg. per administration to the patient.

The medicated compound can be employed in the form of tablets weighing 0.3 g.

The treatment course lasts three weeks at the rate of one tablet three times per day. For terminating, at least temporarily stenocardia attacks, the treatment is carried out once a week at the rate of one tablet three times per day. Disappearance of pain is observed even on the first or second day after the compound has been taken.

The compound can be stored without losing its activity in a place protected from exposure to light.

The present invention also relates to a process for producing the above 10'-($\omega$-N-/1,4-diazabicyclo(4,-m,o)-alkanyl/-acyl)-phenothiazines, and their pharmaceutically acceptable acidic addition and quaternary salts.

To accelerate the reaction a catalyst such as an iodine salt is employed in the process.

The process for producing 10'-($\omega$-N-/1,4-diazabicyclo/-4,m,o/-alkanyl/-acyl)-phenothiazines is effected in accordance with the following scheme:

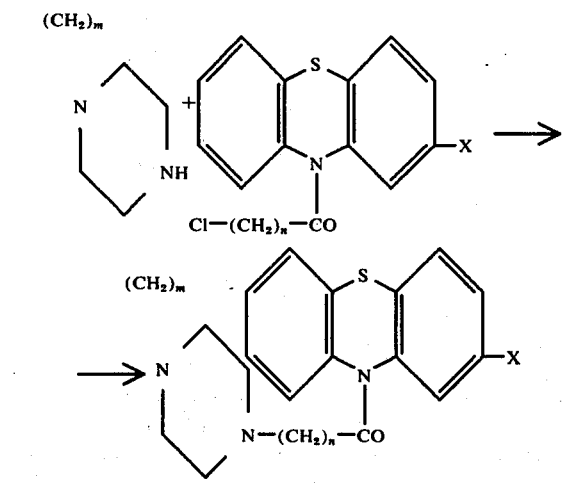

wherein m = 3 or 5; n=1; 2; 3; X = H; Cl; CF$_3$.

The process of condensation of 1,4-diazabicyclo (4,m,o)-alkanes and $\omega$-chloracylphenothiazines is effected in organic solvents which are inactive in respect of the reagents employed (such as benzene, toluene or xylene), the duration of the process being dependent on temperature conditions and adjusted by choosing an appropriate solvent. The process temperature varies generally within the range of from 50° to 140° C; the process duration — from 3 to 20 hours.

To increase the yield of the desired product the reaction is carried out in the presence of basic substances, viz. sodium carbonate or triethylamine, for the purposes of binding the evolving hydrogen chloride.

Tertiary nitrogen atoms of the resulting desired product or an excessive amount of 1,4-diazabicyclo(4,m,o)-alkane can serve as an acceptor for hydrogen chloride evolving during the reaction.

Bis-quaternary salts of said compounds are obtained by treating the resulting bases with an excessive amount of a haloalkyl such as methyl iodide. The isolation of acidic addition salts is effected by conventional techniques.

The yield of the desired products is 40–80% by weight.

For a more complete unerstanding of the present invention reference will now be made to the following specific examples illustrating the process for producing 10'-($\omega$-N-/1,4-diazabicyclo/4,m,o/-alkanyl/-acyl)-phenothiazines and their pharmaceutically acceptable acidic addition and quaternary salts.

EXAMPLE 1

To a solution of 7.2 g of 10-($\beta$-chloropropyonyl)-2-trifluoromethylphenothiazine in 70 ml. of anhydrous toluene, 5.04 g. of 1,4-diazabicyclo-(4,3,0)-nonane are added and the mixture is boiled for three hours. When the heating is stopped, the toluene solution is washed with water and acidified with a diluted solution of hydrochloric acid. The acidic aqueous solution is boiled with activated carbon for 0.5 hour, filtered and the filtrate is rendered alkaline with a 10% caustic soda solution, after which the product is isolated through use of ether. The ether solution is dried by means of magnesium sulphate, and the ether is partially distilled off; the remaining portion of the solution is treated with ether saturated with hydrogen chloride, to yield 7.25 g (69.7% by weight) of 10'-($\beta$-N-(1,4-diazabicyclo(4,3,0)-nonanyl)-propyonyl)-2'-trifluoromethyl-phenothiazine dihydrochloride. M.p. 222°–223° C (in absolution alcohol).

Found: N,8.12%; S,6.23%; Cl',13.38%; $C_{23}H_{26}N_3F_3Cl_2SO$.

Calculated: N,8.07%; S,6.16; Cl',13.62%.

EXAMPLE 2

The reaction is carried out in a manner similar to that described in Example 1, using the same starting reactants employed in equimolar ratio, upon heating in benzene for a period of 16 hours in the presence of triethylamine. The yield of 10'-($\beta$-N-/1,4-diazabicyclo/4,3,0/-nonanyl/-propyonyl/-2'-trifluoromethyl-phenothiazine dihydrochloride is 54% by weight.

EXAMPLE 3

Using a procedure similar to that of Example 1, from 6.48 g of 10-($\beta$-chloropropyonyl)-2-chlorophenothiazine and 5.04 g of 1,4-diazabicyclo(4,3,0)-nonane, 5.82 g (70% by weight of 10'-($\beta$-N-/1,4-diazabicyclo/4,3,0/-nonanyl/-propyonyl/-2'-chlorophenothiazine dihydrochloride are obtained. M.p. 215°–216° C (in absolute alcohol). Found: N, 8.75%; Cl, 21.80%; Cl', 14.38%. $C_{22}H_{26}N_3Cl_3SO$. Calculated: N, 8.63%; Cl, 21.85%; Cl', 14.56%.

EXAMPLE 4

1 g. of 10'-($\beta$-N-/1,4-diazabicyclo/4,3,0/-nonanyl/-propyonyl/)-2'-chlorophenothiazine dihydrochloride is treated with a 40% aqueous caustic soda solution until the pH = 10; the resulting base is extracted with ether; the ether is evaporated; the residue is dissolved in 15 ml. of anhydrous methanol, after which 4.3 g. of methyl iodide are added and the mixture is boiled for 12 hours. Then, methanol is evaporated, and the residue is crystallized from a mixture (1:4) of isopropanol and ethanol.

0.6 g (46% by weight) of 10'-($\beta$-N-)1,4-diazabicyclo/4,3,0/-nonanyl/-propyonyl)-2'-chlorophenothiazine dimethiodide was obtained. M.p. 146°–148° C.

Found: J', 35.93%. $C_{24}H_{30}N_3ClJ_2SO$. Calculated: J', 36.38.

EXAMPLE 5

To a solution of 2.9 g. of 10-($\beta$-chloropropyonyl)-phenothiazine in 40 ml. of anhydrous toluene 2.52 g. of 1,4-diazabicyclo (4,3,0)-nonane are added. The mixture is boiled for 6 hours and treated in a manner similar to that described in Example 1 to yield 2.78 g. (61.5% by weight) of 10'-($\beta$-N-/1,4-diazabicyclo/4,3,0/-nonanyl/-proponyl)phenothiazine, M.p. 190.5°–191.5° C (in absolute alcohol).

Found: S, 7.01%; N, 9.01%; Cl', 15.35%; $C_{22}H_{27}N_3Cl_2SO$. Calculated: S, 7.09%; N, 9.29%; Cl', 15.67%.

EXAMPLE 6

To a solution of 3.1 g of 1-chloracetyl-2-chlorophenethiazine in 40 ml. of anhydrous toluene 2.52 g. of 1,4-diazabicyclo(4,3,0)-nonane are added and the solution is boiled for 6 hours. The toluene solution is washed with water, acidified with a diluted solution of hydrochloric acid; and the aqueous solution is treated with activated carbon, after which the carbon is filtered off and the filtrate is made alkaline.

The product is extracted with ether, the ether solution is dried with magnesium sulphate and the ether is distilled off. 2.97 g. (74% by weight) of 10'-(N-/1,4-diazabicyclo-(4,3,0)-nonanyl/-acetyl)-2'-chlorophenothiazine are thus obtained. M.p. 132.5°–133.5°C.

Found: C, 63.04%; H, 5.57%; Cl, 8.90%; N, 10.35%. $C_{21}H_{22}N_3C_1SO$. Calculated: C, 63.05%; H, 5.54%; Cl, 8.865%; N, 10.51%.

EXAMPLE 7

The reaction is carried out in a manner similar to that described in Example 6. 2 g. of the resulting base 10'-(N-/1,4-diazabicyclo-(4,3,0)-nonanyl/-acetyl)-2'-chlorophenothiazine are dissolved in a small amount of absolute alcohol, after which ether saturated with hydrogen chloride is added thereto. 2 g (84% by weight) of 10'-(N-1,4-diazabicyclo/-4,3,0/-nonanyl/-acetyl)-2'-chlorophenothiazine dihydrochloride are thus produced. M.p. 188°–189.5° C (in absolute alcohol-ether).

Found: Cl',1.467%. $C_{21}H_{24}N_3Cl_3SO$. Calculated: Cl, 15.0%.

EXAMPLE 8

To a solution of 6.76 g of 10-($\gamma$-chlorobutyroyl)-2-chlorophenothiazine in 50 ml. of anhydrous xylene, 5.04 g of 1,4-diazabicyclo(4,3,0)-nonane are added and the mixture is boiled for 15 hours. The xylene solution is decanted the residue is washed with xylene, combined xylene solutions are washed with water and treated with a diluted solution of hydrochloric acid, the water layer is separated, boiled for 20 minutes with activated carbon, after which the carbon is filtered off; the filtrate is rendered alkaline with a 40% caustic soda solution. The product is extracted with ether; the ether extract is dried with magnesium sulphate, the ether is partly filtered off, and the residue is treated with ether saturated with hydrogen chloride. 5.04 g. (50.4% by weight) of 10'-($\gamma$-N-/1,4-diazabicyclo-(4,3,0)-nonanyl/-butyroyl)-2'-chlorophenothiazine dihydrochloride are obtained. M.p. 224°–226° C (in absolute alcohol).

Found: Cl, 21.03%; N, 8.21%; $C_{23}H_{28}N_3Cl_3SO$. Calculated: Cl, 21.23%; N, 8.38%.

EXAMPLE 9

The reaction is carried out in a manner similar to that described in Example 8. The starting products are employed in equimolar amounts and heated in anhydrous toluene in the presence of a two-fold excess of anhydrous sodium carbonate and a catalytic amount of potassium iodide for a period of 20 hours.

Then the mixture is filtered, and the toluene solution is washed with water and further treated according to the procedure of Example 6.

The yield of 10'-(γ-N-/1,4-diazabicyclo(4,3,0)-nonanyl/-butyroyl)-2'-chlorophenothiazine dichlorohydrate is 43% by weight.

EXAMPLE 10

From 10-(β-chloropropyonyl)-2-trifluoromethylphenothiazine and 1,4-diazabicyclo(4,5,0)-undecane, using a procedure similar to that described in Example 1, 10'-(β-N-/1,4-diazabicyclo(4,5,0)-undecanyl/-propyonyl)-2'-trifluoromethylphenothiazine dichlorohydrate is produced. The yield is 64% by weight. The resulting product is a hydrate having one water molecule and possessing no distinct melting temperature.

Found: $H_2O$ 3.5%; Cl', 12.45%; N, 7.25%; S, 5.68%. $C_{25}H_{30}N_3F_3CL_2SO.H_2O$. Calculated: Cl', 12.51%; N, 7.42%; S, 5.66%.

EXAMPLE 11

To the alcoholic solution of 3.4 g of 3.4 g of 10'[β-N/1,4-diazabicyclo [4,3,0] nonanyl) propyonyl]-2'-chlorophenothiazine produced by following the procedure described in Example 3, there is added a solution of 1.3 g of tartaric acid in absolute alcohol. 2.7 g(60 wt.%) of 10'-[β-N-(1,4-diazabicyclo [4,3,0] nonanyl) propyonyl]-2'-chlorophenothiazine tartrate are produced.

Found: C, 53.61%; H, 5.74%; N, 6.73% $C_{26}H_{30}N_3ClSO_7 \cdot H_2O$. Calculated: C, 53.65%; H, 5.54%; N, 7.21%

EXAMPLE 12

To an ether solution of 3.4 g of the base of 10'-[β-N-(1,4-diazabicyclo[4,3,0]-nonanyl) propyonyl]-2'-chlorophenethiazine produced by following the procedure described in Example 3, there is added a solution of 1.9 g of fumaric acid in 40 ml of absolute alcohol, after which the solvent is evaporated dry, the residue is dried, and 4.9 g (94 at %) of 10'-[β-N-(1,4-diazabicyclo[4,3,0]nonanyl)propyonyl]-2'-chlorophenothiazine difumarate are produced. M.p. 157°–159° C.

Found: C, 55.78%; H, 5.32%; N, 6.21%. $C_{30}H_{32}N_3ClSO_9$. Calculated: C, 55.77%; H, 4.99%; N, 6.50.

EXAMPLE 13

To an ether solution of 45 g of the base of 10'-[β-N-(1,4-diazabicyclo[4,3,0]nonanyl)-propyonyl]-2'-chlorophenothiazine, produced by following the procedure described in Example 3, there is added a solution of 2.5 g of maleic acid in 30 ml of absolute alcohol. 5.1 g (72.8 at %) of 10'-[β-N-(1,4-diazabicyclo[4,3,0]nonanyl)-propyonyl]-2'-chlorophenothiazine dimaleate are produced.

Found: C, 55.60%; H, 4.99%; N, 6.71%. $C_{30}H_{32}N_3ClSO_9$. Calculated: C, 55.77%; H, 4.99%; N, 6.50%.

EXAMPLE 14

To an alcoholic solution of 2.7 g of the base of 10'-[β-N-(1,4-diazabicyclo[4,3,0]nonanyl)-propyonyl]-2'-chlorophenothiazine produced by following the procedure described in Example 3, there is added a solution of 1.2 g of 94% sulphuric acid in absolute alcohol. 3 g (81 wt.%) of 10'-[β-N-(1,4-diazabicyclo[4,3,0]-nonanyl)-propyonyl]-2'-chlorophenothiazine disulphate are produced.

Found: C, 43.25; H, 5.04; S, 15.50; N, 6.85; $C_{22}H_{24}N_3ClSO \cdot 2M_2SO_4$. Calculated: C, 43.31; H, 4.63; S, 15.76; N, 6.89.

We claim:

1. A compound selected from the group consisting of a 10'-[ω-N-(1,4-diazabicyclo-[4,m,o]-alkanyl)-acyl]-phenothiazine of the formula:

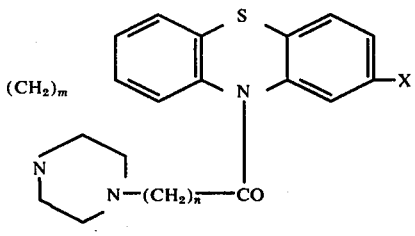

where X is selected from the group consisting of H, Cl, and $CF_3$; n is 1, 2 or 3 and m is 3 or 5, a pharmaceutically acceptable acidic addition salt thereof and a haloalkyl quaternary salt thereof.

2. A phenothiazine according to claim 1 in the free base form.

3. A phenothiazine according to claim 1 in the form of the acid addition salt.

4. A phenothiazine according to claim 1 in the form of the haloalkyl quaternary salt.

5. A phenothiazine according to claim 1 in the form of the quaternary methiodide salt.

* * * * *